(12) United States Patent
Ruhland et al.

(10) Patent No.: US 6,699,864 B2
(45) Date of Patent: Mar. 2, 2004

(54) SUBSTITUTED PHENYL-PIPERAZINE DERIVATIVES, THEIR PREPARATION AND USE

(75) Inventors: Thomas Ruhland, Valby (DK); Christian Krog-Jensen, Copenhagen (DK); Mario Rottländer, Valby (DK); Gitte Mikkelsen, Ballerup (DK); Ejner Knud Moltzen, Gentofte (DK); Kim Andersen, Virum (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 10/177,261

(22) Filed: Jun. 20, 2002

(65) Prior Publication Data

US 2003/0125320 A1 Jul. 3, 2003

Related U.S. Application Data

(63) Continuation of application No. PCT/DK00/00721, filed on Dec. 20, 2000.

(30) Foreign Application Priority Data

Dec. 30, 1999 (DK) .......................... 1999 01885

(51) Int. Cl.⁷ .................. A61K 31/5377; A61K 31/496; C07D 403/06; C07D 487/04
(52) U.S. Cl. .............................. 514/235.8; 514/253.03; 514/254.09; 514/217.05; 514/218; 514/252.11; 514/253.09; 514/254.05; 514/217.08; 514/235.5; 514/323; 514/339; 514/252.13; 514/254.11; 540/575; 540/598; 540/602; 544/121; 544/361; 544/373; 544/357; 544/364; 544/370; 544/371; 544/124; 544/129; 544/376; 546/201; 546/277.4
(58) Field of Search ................. 544/373, 121; 544/361; 514/235.8, 254.09, 253.03

(56) References Cited

U.S. PATENT DOCUMENTS 5,726,177 A 3/1998 Halazy et al. .............. 514/253

FOREIGN PATENT DOCUMENTS

| AU | 81113 B2 | 2/1999 | .......... C07D/333/22 |
| EP | 0 376 607 | 7/1990 | .......... C07D/209/14 |
| GB | 1 326 833 | 8/1973 | ........... C07D/51/70 |
| WO | 94/24105 | 10/1994 | .......... C07D/209/14 |
| WO | 95/14004 | 5/1995 | .......... C07D/209/16 |
| WO | 97/26252 | 7/1997 | ....... C07D/295/033 |
| WO | 99/02516 | 1/1999 | .......... C07D/333/22 |
| WO | 01/49681 A1 * | 7/2001 | |

OTHER PUBLICATIONS

Robichaud et al, Annual Reports in Medicinal Chemistry, vol.35, p.11–20 (2000).*
U.S. patent application Ser. No. 10/187,274, Ruhland et al., filed Jun. 26, 2002.

* cited by examiner

Primary Examiner—Emily Bernhardt
(74) Attorney, Agent, or Firm—Darby & Darby

(57) ABSTRACT

The present invention provides compounds of the formula:

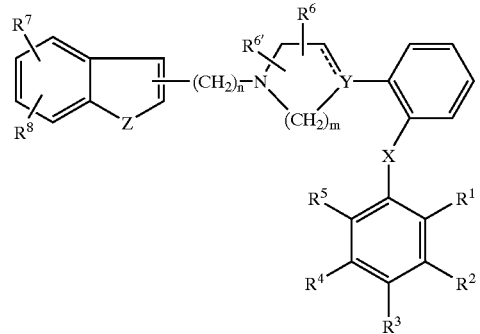

wherein $R^1$-$R^8$, X, Y, Z, n and m are defined in the application.

The compounds of the invention have affinity for the 5-HT$_{1A}$ receptor.

8 Claims, No Drawings

SUBSTITUTED PHENYL-PIPERAZINE DERIVATIVES, THEIR PREPARATION AND USE

This application is a continuation under 35 U.S.C. §120 of International Application No. PCT/DK00/00721, filed Dec. 20, 2000. The prior application is hereby incorporated by reference.

The present invention relates to novel substituted phenyl-piperazine derivatives potently binding to the $5\text{-HT}_{1A}$ receptor, pharmaceutical compositions containing these compounds and the use thereof for the treatment of certain psychiatric and neurological disorders. Many of the compounds of the invention are also potent serotonin reuptake inhibitors and/or $D_3/D_4$ ligands and are thus considered to be particularly useful for the treatment of depression and psychosis.

BACKGROUND ART

Clinical and pharmacological studies have shown that $5\text{-HT}_{1A}$ agonists and partial agonists are useful in the treatment of a range of affective disorders such as generalised anxiety disorder, panic disorder, obsessive compulsive disorder, depression and aggression.

It has also been reported that $5\text{-HT}_{1A}$ ligands may be useful in the treatment of ischaemia.

An overview of $5\text{-HT}_{1A}$ antagonists and proposed potential therapeutic targets for these antagonists based upon preclinical and clinical data are presented by Schechter et al., *Serotottin,* 1997, Vol. 2, Issue 7. It is stated that $5\text{-HT}_{1A}$ antagonists may be useful in the treatment of schizophrenia, senile dementia, dementia associated with Alzheimer's disease, and in combination with SSRI antidepressants also to be useful in the treatment of depression.

5-HT reuptake inhibitors are well known antidepressant drugs and useful for the treatment of panic disorders and social phobia.

The effect of combined administration of a compound that inhibits serotonin reuptake and a $5\text{-HT}_{1A}$ receptor antagonist has been evaluated in several studies (Innis, R. B. et al., *Eur. J. Pharmacol.,* 1987, 143, p 195–204 and Gartside, S. E., *Br. J. Pharmacol.* 1995, 115, p 1064–1070, Blier, P. et al, *Trends Pharmacol. Sci.* 1994, 15, 220). In these studies, it was found that combined $5\text{-HT}_{1A}$ receptor antagonists and scrotonin reuptake inhibitors would produce a more rapid onset of therapeutic action.

Dopamine $D_4$ receptors belong to the dopamine $D_2$ subfamily of receptors, which is considered to be responsible for the antipsychotic effects of neuroleptics. The side effects of neuroleptic drugs, which primarily exert their effect via antagonism of $D_2$ receptors, are known to be due to $D_2$ receptor antagonism in the striatal regions of the brain. However, dopamine $D_4$ receptors are primarily located in areas of the brain other than striatum, suggesting that antagonists of the dopamine $D_4$ receptor will be devoid of extrapyramidal side effects. This is illustrated by the antipsychotic clozapine, which exerts higher affinity for $D_4$ than $D_2$ receptors, and is lacking extrapyramidal side effects (Van Tol et al. *Nature* 1991, 350, 610; Hadley *Medicinal Research Reviews* 1996, 16, 507–526 and Sanner *Exp. Opin. Ther. Patents* 1998, 8, 383–393).

A number of $D_4$ ligands, which were postulated to be selective $D_4$ receptor antagonists (L-745,879 and U-101958) have been shown to posses antipsychotic potential (Mansbach et al. *Psychopharmacology* 1998, 135, 194–200). However, recently it has been reported that these compounds are partial $D_4$ receptor agonists in various in vitro efficacy assays (Gazi et al. *Br. J. Pharmacol.* 1998, 124, 889–896 and Gazi et al. *Br. J. Pharmacol.* 1999, 128, 613–620). Furthermore, it has been shown that clozapine, which is an effective antipsychotic, is a silent antagonists (Gazi et al. *Br. J. Pharmacol.* 1999, 128, 613–620).

Consequently, $D_4$ ligands, which are partial $D_4$ receptor agonists or antagonists, may have beneficial effects against psychoses.

Dopamine $D_4$ antagonists may also be useful for the treatment of cognitive deficits (Jentsch et al. *Psychopharmacology* 1999, 142, 78–84).

It has also been suggested that dopamine $D_4$ antagonists may be useful to reduce dyskinesia occurring as a result of the treatment of Parkinson's disease with L-dopa (Tahar et al. *Eur. J Pharmacol.* 2000, 399, 183–186).

Dopamine $D_3$ receptors also belong to the dopamine $D_2$ subfamily of receptors, and they are preferentially located in limbic regions of the brain (Sokoloff et al. *Nature,* 1990, 347, 146–151), such as the nucleus accumbens, where dopamine receptor blockade has been associated with antipsychotic activity (Willner *Int. Clinical Psychopharmacology* 1997, 12, 297–308). Furthermore, an elevation of the level of $D_3$ receptors in the limbic part of schizophrenic brains has been reported (Gurevich et al. *Arch. Gen. Psychiatry* 1997, 54, 225–32). Therefore, $D_3$ receptor antagonists may offer the potential for an effective antipsychotic therapy, free of the extrapyramidal side effects of the classical antipsychotic drugs, which primarily exert their effect by blockade of $D_2$ receptors (Shafer et al. *Psychopharmacology* 1998, 135, 1–16; Schwartz et al. *Brain Research Reviews* 2000, 31, 277–287).

Moreover, $D_3$ receptor blockade results in a slight stimulation in the prefrontal cortex (Merchant et al. *Cerebral Cortex* 1996, 6, 561–570), which could be beneficial against negative symptoms and cognitive deficits associated with schizophrenia. In addition, dopamine $D_3$ antagonists can reverse $D_2$ antagonist-induced EPS (Millan et al. *Eur. J. Pharmacol.* 1997, 321, R7–R9) and do not cause changes in prolactin (Reavill et al. *J. Pharmacol. Exp. Ther.* 2000, 294, 1154–1165). Consequently, $D_3$ antagonistic properties of an antipsychotic drug could reduce the negative symptoms and cognitive deficits and result in an improved side effect profile with respect to EPS and hormonal changes.

Dopamine $D_3$ agonists have also been considered relevant in the treatment of schizophrenia (Wustow et al. *Current Pharmaceutical Design* 1997, 3, 391–404).

Accordingly, agents acting on the $5\text{-HT}_{1A}$ receptor, both agonists and antagonists, are believed to be of potential use in the therapy of psychiatric and neurological disorders and thus being highly desired. Furthermore, antagonists at the same time having potent serotonin reuptake inhibition activity and/or $D_4$ and/or $D_3$ activity may be particularly useful for the treatment of various psychiatric and neurological diseases.

Structural similar compounds to the compounds of the present invention have been described earlier.

Thiophene derivatives are described in WO 9902516 as ligands for the $5\text{-HT}_{1A}$-receptor.

WO 9726252 describes piperazinyl derivatives as insecticides.

WO 9514004 describes substituted alkylamino-indole derivatives as $5\text{-HT}_{1A}$, $5\text{-HT}_{1B}$ and $5\text{-HT}_{1D}$-derivatives.

It has now been found that compounds of a certain class of phenyl-piperazine derivatives bind to the $5\text{-HT}_{1A}$ receptor with high affinities. Furthermore, it has been found that many of these compounds have other highly beneficial properties as i.e. potent serotonin reuptake inhibition activity and/or affinity for the $D_4$ and/or the $D_3$ receptor.

SUMMARY OF THE INVENTION

Accordingly, the present invention relates to novel compounds of the general Formula I:

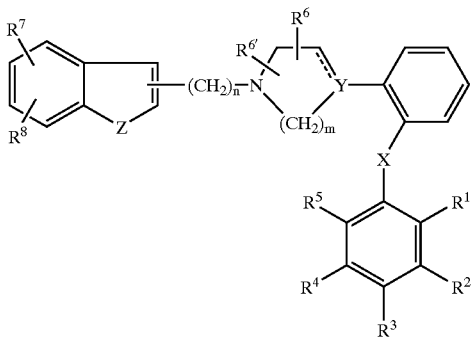

wherein Z represents NH, NR''', O or S; R''' represents hydrogen, $C_{1-6}$-alkyl;

$R^7$ and $R^8$ independently represent hydrogen, halogen, $C_{1-6}$-alkyl, $C_{3-8}$-cycloalkyl, CN, $CF_3$ or $C_{1-6}$-alkoxy; or $R^7$ and $R^8$ together form a 5- or 6-membered aryl or heteroaryl fused to the benzene-ring;

Y represents N, C or CH;

the dotted line represents an optional bond;

$R^6$ and $R^{6'}$ represent H or $C_{1-6}$-alkyl;

X represents —O— or —S— n is 2, 3, 4 or 5;

m is 2 or 3;

$R^1$, $R^2$, $R^3$, $R^4$ and $R^5$ are independently selected from a group consisting of hydrogen, halogen, $C_{1-6}$-alkyl, $C_{1-6}$-alkenyl, $C_{1-6}$-alkynyl, $C_{3-8}$-cycloalkyl, aryl, hydroxy, hydroxy-$C_{1-6}$-alkyl, $C_{1-6}$-alkoxy, $C_{3-8}$-cycloalkoxy, $C_{1-6}$-alkylsulfanyl, acyl, $NR^9R^{10}$ wherein $R^9$ and $R^{10}$ independently represent hydrogen, $C_{1-6}$-alkyl, $C_{2-6}$-alkenyl, $C_{2-6}$-alkynyl, $C_{3-8}$-cycloalkyl or aryl; or $R^9$ and $R^{10}$ together with the nitrogen to which they are attached form a 1-morpholinyl, 1-piperidinyl, 1-homopiperidinyl, 1-piperazinyl, 1-homopiperazinyl, 1-imidazolyl, 1-pyrrolyl, or pyrazolyl, all of which may be further substituted with $C_{1-6}$-alkyl; or two adjacent substituents of $R^1$–$R^5$ together form a ring fused to the phenyl ring selected from the group consisting of

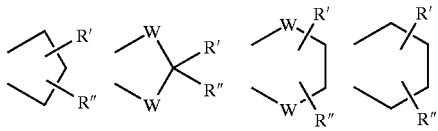

wherein W is O or S, and R' and R'' are hydrogen or $C_{1-6}$-alkyl:

The compounds of the invention have affinity for the 5-$HT_{1A}$ receptor. Accordingly, the invention provides:

A compound as above as a medicament.

A pharmaceutical composition comprising at least one compound of Formula I as defined above or a pharmaceutically acceptable acid addition salt thereof or prodrug thereof in a therapeutically effective amount and in combination with one or more pharmaceutically acceptable carriers or diluents.

The present invention provides the use of a compound of Formula I as defined above or an acid addition salt or prodrug thereof for the manufacture of a pharmaceutical preparation for the treatment of the above mentioned disorders.

The invention provides a method for the treatment of diseases and disorders in humans caused by abnormalities in the serotonin system of the central nervous system comprising the administration of an effective amount of a compound of Formula I as above.

The compounds of the invention are considered useful for the treatment of affective disorders, such as depression, generalised anxiety disorder, panic disorder, obsessive compulsive disorders, social phobia, and eating disorders, psychosis and neurological disorders such as ischacemia and senile dementia.

DETAILED DESCRIPTION OF THE INVENTION

A preferred embodiment of the invention is the compound of formula I as above wherein Z is NH and the resulting indole is connected in position 3;

Another preferred embodiment of the invention is the compound of formula I as above wherein $R^7$ and $R^8$ independently are selected from a hydrogen, halogen, $C_{1-6}$-alkyl or $R^7$ and $R^8$ together form a fused pyridyl-ring;

Another preferred embodiment of the invention is the compound of formula I as above wherein n is 2, 3 or 4;

Another preferred embodiment of the invention is the compound of formula I as above wherein m is 2;

Another preferred embodiment of the invention is the compound of formula I as above wherein $R^6$ and $R^{6'}$ are both hydrogen;

Another preferred embodiment of the invention is the compound of formula I as above wherein Y is N;

Another preferred embodiment of the invention is the compound of formula I as above wherein $R^1$, $R^2$, $R^3$, $R^4$ and $R^5$ are independently selected from hydrogen, alkoxy, $NR^3R^4$ wherein $R^3$ and $R^4$ independently represent hydrogen, $C_{1-6}$-alkyl; or $R^3$ and $R^4$ together form a 1-morpholino; or two of adjacent of $R^1$, $R^2$, $R^3$, $R^4$ and $R^5$ together form a fused ring consisting of

—O—$CH_2$—O—,

—O—$CH_2$—$CH_2$—O—, or

—$CH_2$—$CH_2$—$CH_2$—;

Another preferred embodiment of the invention is the compound of formula I as above wherein one or two of $R^1$, $R^2$, $R^3$, $R^4$, $R^5$ are not hydrogen;

The most preferred embodiment of the invention is the compound according to formula I as above, the compound being:

1-{1-[3-(dimethylamino)phenoxy]phenyl}-4-[2-(1H-indol-3-yl)ethyl]piperazine;

1-[1-(1,3-Benzodioxolan-5-yloxy)phenyl]-4-[2-(1H-indol-3-yl)ethyl]piperazine;

1-{1-[3-(dimethylamino)phenoxylphenyl}-4-[3-(1H-indol-3-yl)propyl]piperazine;

1-[1-(1,3-Benzodioxolan-5-yloxy)phenyl]-4-[3-(1H-indol-3-yl)propyl]piperazine;

1-[2-(1,3-Benzodioxolan-5-yloxy)phenyl]-4-[3-(6-chloro-1H-indol-3-yl)propyl]piperazine, 1-[2-(2-Methoxyphenoxy)phenyl]-4-[3-(5-fluoro-1H-indol-3-yl)propyl]piperazine, 1-[2-(1,4-Benzodioxan-6-yloxy)phenyl]-4-[3-(1H-indol-3-yl)propyl]piperazine 1-[2-(1,4-Benzodioxan-5-yloxy)phenyl]-4-[3-(5-fluoro-1H-indol-3-yl)propyl]piperazine 1-[2-(1,4-Benzodioxan-5-yloxy)phenyl]-4-[3-(6-chloro-1H-indol-3-yl)propyl]piperazine 1-[2-(1,4-Benzodioxan-6-yloxy)phenyl]4-[3-(6-chloro-1H-indol-3-yl)propyl]piperazine 1-[2-(2-Methoxyphenoxy)phenyl]-4-[3-(6-chloro-1H-indol-3-yl)propyl]piperazine 1-[2-(3-Methoxyphenoxy)phenyl]-4-[3-(6-chloro-1H-indol-3-yl)propyl]piperazine 1-[2-(2-Methoxyphenoxy)phenyl]-4-[3-(1H-indol-3-yl) propyl]piperazine;
1-(2-Phenoxyphenyl)-4-[4-(1H-indol-3-yl)butyl] piperazine;
1-[2-(1,3-Benzodioxolan-5-yloxy)phenyl]-4-[4-(1H-indol-3-yl)butyl]piperazine;
1-[2-(2-Methoxyphenoxy)phenyl]-4-[2-(6-chloro-1H-indol-3-yl)ethyl]piperazine;
1-[2-(1,3-Benzodioxolan-5-yloxy)phenyl]-4-[2-(6-chloro-1H-indol-3-yl)ethyl]piperazine;
1-[2-(3-(Dimethylamino)phenoxy)phenyl]-4-[2-(6-chloro-1H-indol-3-yl)ethyl]piperazine;
1-[2-(2-Methoxyphenoxy)phenyl]-4-[4-(1H-indol-3-yl)butyl]piperazine;
1-[2-(4-Methoxyphenoxy)phenyl]-4-[3-(1H-indol-3-yl)propyl]piperazine;
1-[2-(3-(Dimethylamino)phenoxy)phenyl]-4-[4-(1H-indol-3-yl)butyl]piperazine;
1-(2-Phenoxyphenyl)-4-[2-(6-chloro-1H-indol-3-yl) ethyl]piperazine;
1-[2-(1,4-Benzodioxan-5-yloxy)phenyl]-4-[3-(5-fluoro-1H-indol-3-yl)propyl]piperazine;
1-(2-Phenoxyphenyl)-4-[3-(5-methyl-1H-indol-3-yl) propyl]piperazine;
1-[2-(2-Methoxyphenoxy)phenyl]-4-[3-(5-chloro-1H-indol-3-yl)propyl]piperazine;
1-[2-(2-Methoxyphenoxy)phenyl]-4-[3-(5-bromo-1H-indol-3-yl)propyl]piperazine;
1-(2-Phenoxyphenyl)-4-[3-(1H-indol-3-yl)propyl] piperazine;
1-(2-Phenoxyphenyl)-4-[3-(5-fluoro-1H-indol-3-yl) propyl]piperazine;
1-(2-Phenoxyphenyl)-4-[3-(5-bromo-1H-indol-3-yl) propyl]piperazine;
1-[2-(2,6-Dimethoxyphenoxy)phenyl]-4-[3-(5-bromo-1H-indol-3-yl)propyl]piperazine;
1-[2-(3-(Dimethylamino)phenoxy)phenyl]-4-[3-(5-methyl-1H-indol-3-yl)propyl]piperazine;
1-(2-Phenoxyphenyl)-4-[3-(5-chloro-1H-indol-3-yl) propyl]piperazine;
1-[2-(1,3-Benzodioxolan-5-yloxy)phenyl]-4-[3-(5-methyl-1H-indol-3-yl)propyl]piperazine;
1-[2-(2-Methoxyphenoxy)phenyl]-4-[3-(5-fluoro-1H-indol-3-yl)propyl]piperazine;
1-[2-(2-Methoxyphenoxy)phenyl]-4-[3-(7-chloro-1H-indol-3-yl)propyl]piperazine;
1-[2-(1,3-Benzodioxolan-5-yloxy)phenyl]-4-[3-(5-fluoro-1H-indol-3-yl)propyl]piperazine;
1-[2-(1,3-Benzodioxolan-5-yloxy)phenyl]-4-[3-(5-iodo-1H-indol-3-yl)propyl]piperazine;
1-(2-Phenoxyphenyl)-4-[3-(7-chloro-1H-indol-3-yl) propyl]piperazine;
1-(2-Phenoxyphenyl)-4-[3-(5,7-difluoro-1H-indol-3-yl) propyl]piperazine
1-[2-(2-Methoxyphenoxy)phenyl]-4-[3-(7-bromo-1H-indol-3-yl)propyl]piperazine;
1-[2-(3-(Dimethylamino)phenoxy)phenyl]-4-[3-(5-fluoro-1H-indol-3-yl)propyl]piperazine;
1-[2-(2-Methoxyphenoxy)phenyl]-4-[3-(5-iodo-1H-indol-3-yl)propyl]piperazine;
1-[2-(1,3-Benzodioxolan-5-yloxy)phenyl]-4-[3-(5-chloro-1H-indol-3-yl)propyl]piperazine;
1-[2-(2,6-Dimethoxyphenoxy)phenyl]-4-[3-(5-chloro-1H-indol-3-yl)propyl]piperazine;
1-[2-(1,3-Benzodioxolan-5-yloxy)phenyl]-4-[3-(1H-pyrrolo[3,2-h]quinolin-3-yl)propyl]piperazine;
1-[2-(2-Methoxyphenoxy)phenyl]-4-[3-(5,7-difluoro-1H-indol-3-yl)propyl]piperazine;
1-(2-Phenoxyphenyl)-4-[3-(5-iodo-1H-indol-3-yl)propyl] piperazine;
1-[2-(2-Methoxyphenoxy)phenyl]-4-[3-(1H-pyrrolo[3,2-h]quinolin-3-yl)propyl]piperazine;
1-[2-(3-Methoxyphenoxy)phenyl]-4-[3-(1H-pyrrolo[3,2-h]quinolin-3-yl)propyl]piperazine;
1-[2-(1,4-Benzodioxan-5-yloxy)phenyl]-4-[3-(5-methyl-1H-indol-3-yl)propyl]piperazine;
1-[2-(2,6-Dimethoxyphenoxy)phenyl]-4-[3-(5-methyl-1H-indol-3-yl)propyl]piperazine;
1-[2-(3-Methoxyphenoxy)phenyl]-4-[3-(1H-indol-3-yl) propyl]piperazine;
1-[2-(1,4-Benzodioxan-5-yloxy)phenyl]-4-[3-(1H-indol-3-yl)propyl]piperazine;
1-[2-(1,3-Benzodioxolan-5-yloxy)phenyl]-4-[3-(5-bromo-1H-indol-3-yl)propyl]piperazine;
1-{2-[3-(Morpholin-4-yl)phenoxy]phenyl}-4-[3-(5-fluoro-1H-indol-3-yl)propyl]piperazine;
1-[2-(3-Methoxyphenoxy)phenyl]-4-[3-(5-chloro-1H-indol-3-yl)propyl]piperazine;
1-[2-(3-Ethoxyphenoxy)phenyl]-4-[3-(5-methyl-1H-indol-3-yl)propyl]piperazine;
1-[2-(2,6-Dimethoxyphenoxy)phenyl]-4-[3-(5-iodo-1H-indol-3-yl)propyl]piperazine;
1-[2-(3-(Diethylamino)phenoxy)phenyl]-4-[3-(5-fluoro-1H-indol-3-yl)propyl]piperazine;
1-[2-(2,6-Dimethoxyphenoxy)phenyl]-4-[3-(5-fluoro-1H-indol-3-yl)propyl]piperazine;
1-{2-[3-(Morpholin-4-yl)phenoxy]pbenyl}-4-[3-(5-bromo-1H-indol-3-yl)propyl]piperazine;
1-{2-[3-(Morpholin-4-yl)phenoxy]phenyl}-4-[3-(5-chloro-1H-indol-3-yl)propyl]piperazine;
1-{2-[3-(Morpholin-4-yl)phenoxy]phenyl}-4-[3-(5-iodo-1H-indol-3-yl)propyl]piperazine;
1-[2-(3-Methoxyphenoxy)phenyl]-4-[3-(7-fluoro-1H-indol-3-yl)propyl]piperazine;
1-(2-Phenoxyphenyl)-4-[3-(5,7-dimethyl-1H-indol-3-yl) propyl]piperazine;
1-[2-(1,3-Benzodioxolan-5-yloxy)phenyl]-4-[3-(7-bromo-1H-indol-3-yl)propyl]piperazine;
1-[2-(3,4,5-Trimethoxyphenoxy)phenyl]-4-[3-(5-bromo-1H-indol-3-yl)propyl]piperazine;

Some of the compounds of general Formula I may exist as optical isomers thereof and such optical isomers are also embraced by the invention.

The term $C_{1-6}$ alkyl refers to a branched or unbranched alkyl group having from one to six carbon atoms inclusive, such as methyl, ethyl, 1-propyl, 2-propyl, 1-butyl, 2-butyl, 2-methyl-2-propyl and 2-methyl-1-propyl.

Similarly, $C_{2-6}$ alkenyl and $C_{2-6}$ alkynyl, respectively, designate such groups having from two to six carbon atoms, inclusive and the groups are having at least one double bond or triple bond respectively;

Halogen means fluoro, chloro, bromo, or iodo.

The term $C_{3-8}$-cycloalkyl designates a monocyclic or bicyclic carbocycle having three to eight C-atoms, such as cyclopropyl, cyclopentyl, cyclohexyl, cycloheptyl, and cyclooctyl. Preferred embodiments are cyclopropyl, cyclopentyl, cyclohexyl.

The terms $C_{1-6}$ alkoxy, $C_{1-6}$ alkylsulfanyl, $C_{3-8}$-cycloalkoxy, designate such groups in which the alkyl group is $C_{1-6}$ alkyl as defined above.

Acyl means CHO and —CO-alkyl wherein the alkyl group is $C_{1-6}$ alkyl as defined above.

5- or 6-membered rings which are aryl or heteroaryl designates groups such as phenyl, pyrrolyl, pyridyl, pyrimidyl, furanyl, thienyl;

Exemplary of organic acid addition salts according to the invention are those with maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic, and theophylline acetic acids, as well as the 8-halotheophyllines, for example 8-bromotheophylline. Exemplary of inorganic acid addition salts according to the invention are those with hydrochloric, hydrobromic, sulfuric, sulfamic, phosphoric, and nitric acids. The acid addition salts of the invention are preferably pharmaceutically acceptable salts formed with non-toxic acids.

Furthermore, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

Some of the compounds of the present invention contain chiral centres and such compounds exist in the form of isomers (e.g. enantiomers). The invention includes all such isomers and any mixtures thereof including racemic mixtures.

Racemic forms can be resolved into the optical antipodes by known methods, for example, by separation of diastereomeric salts thereof with an optically active acid, and liberating the optically active amine compound by treatment with a base. Another method for resolving racemates into the optical antipodes is based upon chromatography on an optically active matrix. Racemic compounds of the present invention can thus be resolved into their optical antipodes, e.g., by fractional crystallisation of d- or 1- (tartrates, mandelates, or camphorsulphonate) salts for example. The compounds of the present invention may also be resolved by the formation of diastereomeric derivatives.

Additional methods for the resolution of optical isomers, known to those skilled in the art, may be used. Such methods include those discussed by J. Jaques, A. Collet, and S. Wilen in "Enantiomers, Racemates, and Resolutions", John Wiley and Sons, New York (1981).

Optically active compounds can also be prepared from optically active starting materials.

The compounds of the invention can be prepared by one of the following methods comprising:

a) reacting a secondary amine of the formula

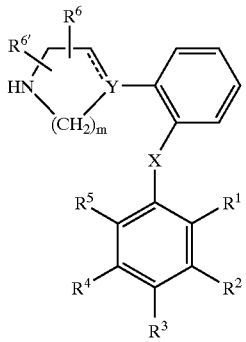

III wherein $R^1$–$R^{6'}$, X, Y and m are as defined above with an alkylating agent of the general formula:

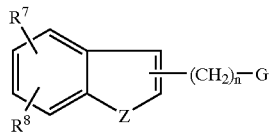

and $R^7$, $R^8$, Z and n are as defined above and G is a suitable leaving group such as halogen, mesylate or tosylate;

b) reacting a compound of the formula

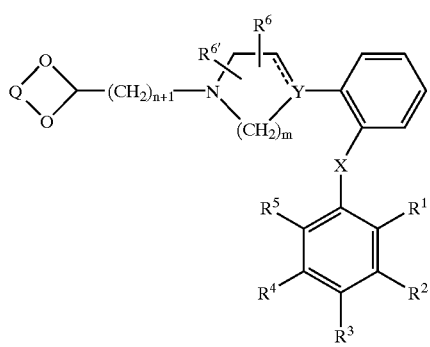

IV wherein $R^1$–$R^{6'}$, X, Y, n and m are as defined above and $Q(OH)_2$ is a diol such as substituted ethylene glycol or propylene glycol or a polymer bound diol;

with a hydrazine of the formula

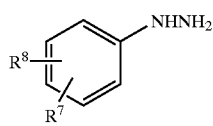

V c) reducing an amide of formula

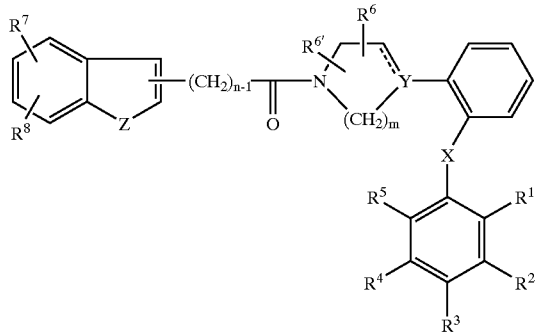

VI wherein Z, $R^1$–$R^8$, X, Y, n and in are as defined above.

d) reducing a compound of formula

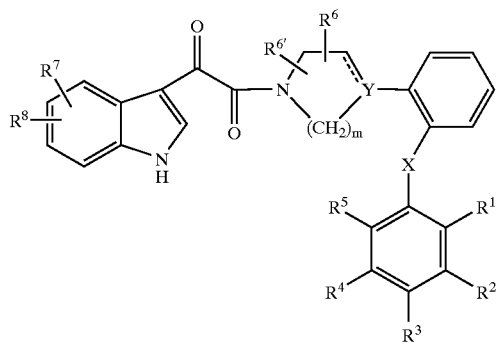

VII wherein $R^1$–$R^8$, Y, X and in are as defined above

The alkylations according to method a are generally performed by boiling the reactants under reflux or by heating them at a fixed temperature in a suitable solvent such as acetone, acetonitrile, methyl isobutyl ketone, tetrahydrofuran, dioxane, ethanol, 2-propanol, ethyl acetate, N,N-dimethylformamide, dimethyl sulfoxide or 1-methyl-2-pyrrolidinone in the presence of a base such as triethylamine or potassium carbonate and optionally a catalytic amount of potassium iodide.

1)

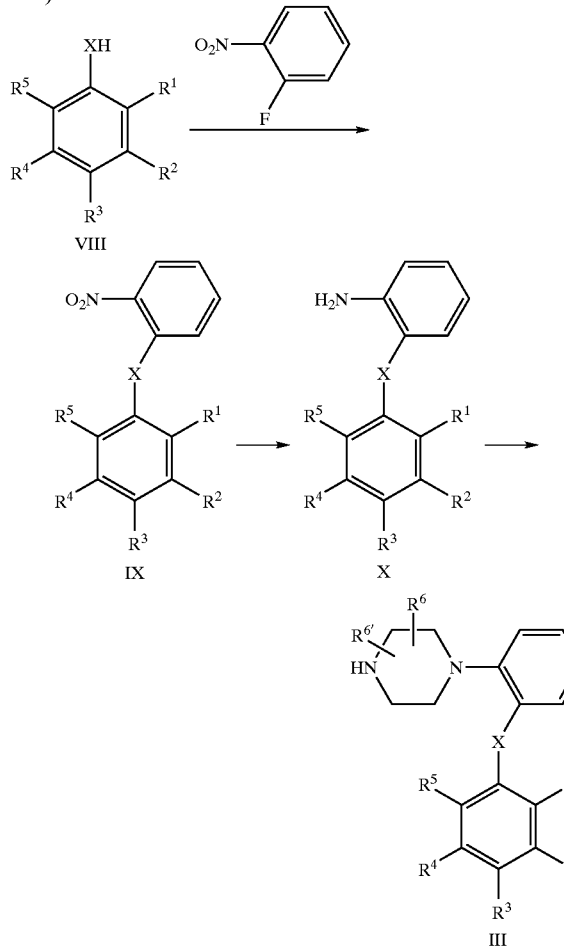

solvent such as N,N-dimethylformamide using organic or inorganic basis at elevated temperature. After reduction of the intermediate nitro compound IX using standard conditions such as palladium catalysed hydrogenation or iron in acidic solvents, the aniline derivative X was transformed into the desired secondary amine of formula III. The piperazine formation was either performed by reaction with bis(2-chloroethyl)amine, hydrochloride at elevated temperature or in a multistep synthesis according to published procedures (Kruse et al., Recl. Trav. Chim. Pays-Bas, 1988, 107, 303–309).

2)

Secondary amines of formula III are prepared by the reaction sequence outlined above. 2-Fluoro-nitrobenzene is reacted with a nucleophile of formula VIII in an aprotic Alternatively, secondary amines of formula III are prepared using the mono substituted cyclic diamines of formula XII as key intermediate. The substituent R is an appropriate protecting group such as a ethoxy-, methoxy- or 2-methyl-2-propyloxy-carbonyl group or a benzyl group, or a suitable solid support such as a Merrifield resin or a solid supported carbamate group such as the wang resin based carbamate linker (Zaragoza, Tetrahedron Lett., 1995, 36, 8677–8678). The mono substituted cyclic diamines of formula XII are prepared from commercially available starting materials or by methods obvious to the chemist skilled in the art. The mono substituted cyclic diamine of formula XII are reacted with $\eta^6$-1,2-dichlorobezene-$\eta^5$-cyclopentadienyliron(II) hexafluorophosphate at elevated temperature in an aprotic solvent such as dry tetrahydrofuran using an appropriate base such as potassium carbonate. $\eta^6$-1,2-dichlorobezene-$\eta^5$-cyclopentadienyliron(II) hexafluorophosphate are prepared in analogy to literature procedures (Pearson and Gelormani, J. Org. Chem. 1994, 59, 4561–4570). The thus formed mono chloro derivative of formula XIII are subsequently reacted with a nucleophile of formula VIII in an aprotic solvent such as dry tetrahydrofuran either by the use of an appropriate base such as potassium carbonate or by deprotonation of the nucleophile of formula VIII using a base such as sodium hydride prior to the reaction. Decomplexation, performed according to literature procedures (Pearson et al., J. Org. Chem. 1996, 61, 1297–1305), followed by deprotection by methods obvious to the chemist skilled in the art or cleavage from the solid support according to literature procedures (Zaragoza, Tetrahedron Lett., 1995, 36, 8677–8678 and Conti et al., Tetrahedron Lett., 1997, 38, 2915–2918) afforded the desired secondary amines of formula III, corresponding to secondary amines of formula XV, R. H. Nucleophiles of formula VIII are commercially available, prepared by methods obvious to the chemist skilled in the art or according to literature procedures (Guillaumet and Hretani, J. Heterocyclic Chem., 26, 193–196, 1989).

The alkylating agents of formula

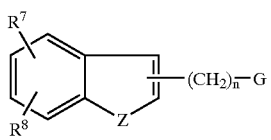

are prepared according literature procedures (J. Med. Chem. 1983, 26, 1470–1477, Brodfuehrer et al., J. Org. Chem. 1997, 62, 9192–9202, Anelli, et al., J. Org. Chem. 1987, 52, 2559–2562, Brodfuehrer, et al., J. Org. Chem. 1997, 62, 9192–9202) or by methods obvious to the chemist skilled in the art.

The indole formation according to method b is performed by the reaction of acetals of formula IV with aryl hydrazines of formula V resulting in the corresponding hydrazones, which subsequently are converted into indoles by means of the Fischer indole synthesis. The synthesis sequence is preferably performed as a one-pot procedure using a Lewis acid catalysts, preferably zinc chloride or boron trifluoride, or protic acids, preferably sulfuric acid or phosphoric acid, in a suitable solvent such as acetic acid or ethanol at an elevated temperature.

Acetals of formula IV are prepared by the reaction sequence 2) outlined above using mono substituted cyclic diamines of formula XII wherein

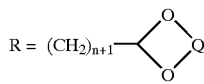

as key intermediates. The key intermediates of formula XII are prepared by alkylation of cyclic diamines of formula XI with acetals of formula

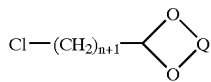

XVI using the conditions described above for methods a.

Polymer bound acetals of formula XVI are prepared by reaction of aldehydes of formula G—$(CH_2)_{n+1}$—CHO with commercially available 2,2-dimethyl-1,3-dioxolan-4-yl-methoxymethyl polystyrene in a suitable solvent such as toluene, using p-toluenesulfonic acid as catalyst at elevated temperature. 4-Chlorobutanal, 5-chloropentanal, and 6-chlorohexanal were prepared in analogy to the method described by Normant et al., Tetrahedron 1994, 50 (40), 11665.

The reductions according to Method c and d are generally performed by use of $LiAlR_4$, $AlH_3$ or diborane in an inert solvent such as tetrahydrofuran, dioxane, or diethyl ether at room temperature or at a slightly elevated temperature. The amides of formula VI are prepared from secondary amines of formula III and a substituted indol-3-ylalkylcarboxylic acids or carboxylic acid chlorides by methods obvious to the chemist skilled in the art. The amides of formula VII are prepared from 3-unsubstituted indoles and secondary amines of formula III according to literature multistep procedures (Nichols al., Synthesis 1999, 6, 935–938 and Speeter and Anthony, J. Am. Chem. Soc. 1954, 76, 6208–6210)

EXAMPLES

All reactions were carried out under a positive pressure of nitrogen. Melting points were determined on a Buchi SMP-20 apparatus and are uncorrected.

Analytical LC-MS data were obtained on a PE Sciex API 150EX instrument equipped with IonSpray source and Shimadzu LC-8A/SLC-IOA LC system. The LC conditions (50×4.6 mm YMC ODS-A with 5 μm particle size) were linear gradient elution with water/acetonitrile/trifluoroacetic acid (90:10:0.05) to water/acetonitrile/trifluoroacetic acid (10:90:0.03) in 7 min at 2 ml/min. For compounds 3c, 3e, 3f, and 3l, the LC conditions (Waters Symmetry, 30×4.6 mmm, C18 3.5 my particle size) were linear gradient elution with water/acetonitrile/trifluoroacetic acid (90:10:0.05) to water/acetonitrile/trifluoroacetic acid (10:90:0.03) in 4 min at 2 ml/min. Purity was determined by integration of the UV trace (254 nm). The retention times $R_1$ are expressed in minutes.

Preparative LC-MS-separation was performed on the same instrument. The LC conditions (50×20 mm YMC ODS-A with 5 μm particle size) were linear gradient elution with water/acetonitrile/trifluoroacetic acid (80:20:0.05) to water/acetonitrile/trifluoroacetic acid (10:90:0.03) in 7 min at 22.7 mL/min. Fraction collection was performed by split-flow MS detection.

$^1$H NMR spectra were recorded at 500.13 MHz on a Bruker Avance DRX500 instrument or at 250.13 MHz on a Bruker AC 250 instrument. Deuterated chloroform (99.8% D) or dimethyl sulfoxide (99.9% D) were used as solvents. TMS was used as internal reference standard. Chemical shift values are expressed in ppm-values. The following abbreviations are used for multiplicity of NMR signals: s=singlet, d=doublet, t=triplet, q=quartet, qui=quintet, h=heptet, dd=double doublet, dt=double triplet, dq=double quartet, tt=triplet of triplets, m=multiplet and b=broad singulet. NMR signals corresponding to acidic protons are generally omitted.

Content of water in crystalline compounds was determined by Karl Fischer titration. Standard workup procedures refer to extraction with the indicated organic solvent from proper aqueous solutions, drying of combined organic extracts (anhydrous $MgSO_4$ or $Na_2SO_4$), filtering and evaporation of the solvent in vacuo. For column chromatography, silica gel of type Kieselgel 60, 230–400 mesh ASTM was used. For ion-exchange chromatography, the following material was used: SCX-columns (1 g) from Varian Mega Bond Elut®, Chrompack cat. No. 220776. Prior use the SCX-columns were pre-conditioned with 10% solution of acetic acid in methanol (3 mL). For reversed phase chromatography, the following material was used: C-18 columns (I g) from Varian Mega Bond Elut®, Chrompack cat. No. 220508). Prior use the C-18-columns were pre-conditioned with methanol (3 mL) and water (3 mL). For decomplexation by irradiation, a ultaviolet light source (300 W) from Philipps was used.

Example 1

1–2-[3-(Dimetelylamino)Phenoxy]Phenyl)-4-[2-(1H-Indol-3-Yl)Ethyl]Piperazine, Oxalate (1a).

1-Chloro-2-nitrobenzene (15.0 g), 3-(dimethylamino) phenol (13.0 g) and potassium hydroxide (11.8 g) was dissolved in N,N-dimethylformamide (350 mL) and boiled under reflux for 18 hrs. The reaction was then cooled, and poured into water, and worked up by standard procedure using ethyl acetate. The crude product was purified by silicagel chromatography (heptane:ethyl acetate:triethylamine/80:10:10). The pure intermediate was dissolved in a mixture of ethanol (200 mL) and acetic acid (20 mL). After addition of Pd/C (5%, 4.5 g), the reaction mixture was shaken under hydrogen atmosphere (3 bar) for 3 hrs. The reaction mixture was filtered and after neutralisation worked up by standard procedure using ethyl acetate affording pure aniline (11.2 g). The crude aniline, bis-(2-chloroethyl)amine hydrochloride (8.6 g) and chlorobenzene (200 mL) was boiled under reflux for 48 hrs. The reaction mixture was cooled to room temperature, and the volatile solvents evaporated in vacuo to give the crude 1-{[3-(dimethylamino)phenoxy]phenyl}piperazine (18.6 g). A solution of the crude piperazine, di-tert-butyl dicarbonate (32 g) and potassium carbonate (68 g) in tetrahydrofuran:water/1:1, was heated at 50° C. for 18 hrs. The organic layer was separated and the water phase extracted with ethyl acetate. The collected organic phases were worked up by standard procedure followed by purification by silicagel chromatography (heptane:ethyl acetate/8:2) affording pure BOC-protected 1-{[3-dimethyl)phenoxy]phenyl}piperazine (9.4 g). A solution of the BOC-derivative in a mixture of dry THF (30 mL) and trifluoroacetic acid (30 mL) was stirred at room temperature for 1 h. The volatile solvents were evaporated in vacuo and ethyl acetate and 1 N aqueous sodium hydroxide were added. The organic phase was collected and worked up by standard procedure giving pure 1-{[3-(dimethylamino) phenoxy]phenyl}piperazine (6.0 g). A mixture of a part of the pure piperazine (1.37 g), 3-(2-bromoethyl)-1H-indole (1.0 g), potassium carbonate (2.2 g), potassium iodide (cat.) and methyl isobutyl ketone was boiled under reflux for 24 hrs. The mixture was cooled to room temperature, filtered, and the volatile solvents evaporated in vacuo to give an oil which was purified by silicagel chromatography (heptane:ethyl acetate:triethylamine/26:70:4) to give the title compound as an oil. The title compound was crystallised as its oxalate from acetone (1.27 g). Mp 210–203° C. $^1$H NMR/250 MHz (DMSO-$d_6$): 2.85 (s, 6H); 3.00–3.35 (m, 12H); 6.15 (d, 1H); 6.35 (s, 1H); 6.45 (d, 1H); 6.85 (d, 1H); 6.95–7.15 (m, 6H); 7.20 (s, 1H); 7.35 (d, 1H); 7.55 (d, 1H); 10.90 (s, 1H). MS: m/z: 441 (MH+), 144. Anal. Calcd. for $C_{28}H_{32}N_4O$: C, 67.89; H, 6.47; N, 10.56. Found C, 67.34; H, 6.59; N, 10.30.

The following compounds were prepared using the same general method:

1-[2-(1,3-Benzodioxolan-5-yloxy)phenyl]-4-[2-(1H-indol-3-yl)ethyl]piperazine, oxalate (1b). Mp 221–228° C. $^1$H NMR (250 MHz, DMSO-$d_6$): 3.00–3.35 (m, 12H); 6.00 (s, 2H); 6.40 (dd, 1H); 6.65 (d, 1H); 6.80–6.90 (m, 2H); 6.95–7.15 (m, 5H); 7.20 (d, 1H); 7.35 (d, 1H); 7.55 (d, 1H); 10.90 (s, 1H). MS: m/z: 443 (MH+), 311, 131. Anal. Calcd. For $C_{27}H_{27}N_3O_3$: C, 65.10; H, 5.54; N, 7.86. Found C, 64.86; H, 5.55; N, 7.60.

Example 2

1-{2-[3-(Dimethylamino)Phenoxy]Phenyl}-4-[3-(1H-Indol-3-Yl)Propyl]Piperazine (2a).

To a suspension of litium aluminum hydride (8.0 g) in tetrahydrofuran (500 mL) was a solution of 3-indolepropionic acid (20 g) in tetrahydrofuran (100 mL) added dropwise. The reaction mixture was stirred for 1 h at room temperature and subsequently cooled to 5° C. After sequential addition of water (16 mL), 15% aqueous sodium hydroxide (8.0 mL) and water (40 mL), the reaction mixture was stirred at room temperature over night and filtered. Evaporation of the volatile solvents gave pure 3-(1H-indol-3-yl)propanol (19.1 g) as an oil. 3-(1H-Indol-3-yl)propanol (18.6 g) and carbon tetrabromide (42.1 g) was dissolved in acetonitrile (1 L) and cooled to 0° C. and triphenylphosphine (30.7 g) was added in small portions. The reaction was stirred for further 3 h at room temperature, the volatile solvents evaporated in vacuo and the remaining oil purified by silicagel chromatography (heptane:ethyl acetate/2:1) to give 3-(3-bromopropyl)-1H-indole (25.6 g).

This intermediate was coupled to the piperazine moieties using the method described in Example 1 to give the title compound isolated as an amorphous solid. $^1$H NMR (250 MHz, DMSO-$d_6$): 1.80 (q, 2H); 2.25–2.40 (m, 6H); 2.65 (t, 2H); 2.85 (s, 6H); 3.05 (m, 4H); 6.10 (dd, 1H); 6.30 (t, 1H); 6.45 (dd, 1H); 6.80–7.10 (m, 8H); 7.30 (d, 1H); 7.50 (d, 1H); 10.70 (b, 1H). MS: m/z: 455 (MH+), 295, 239, 201, 130.

The following compounds were prepared analogously:

1-[2-(1,3-Benzodioxolan-5-Yloxy)Phenyl]-4-[3-(1H-Indol-3-Yl)Propyl]Piperazine, Oxalate (2b). Mp 156–162° C. $^1$H NMR (250 MHz, DMSO-$d_6$): 1.80 (q, 2H); 2.25–2.40 (m, 6H); 2.70 (t, 2H); 3.05 (m, 4H); 6.00 (s, 2H); 6.35 (dd, 1H); 6.55 (d, 1H); 6.85 (d, 2H); 6.90–7.15 (m, 6H); 7.30 (d, 1H); 7.50 (d, 1H); 10.75 (s, 1H). MS: m/z: 456 (MH+), 297, 201, 130. Anal. Calcd. For $C_{28}H_{29}N_3O_3$: C, 73.81; H, 6.43; N, 9.23. Found C, 73.28; H, 6.45; N, 9.00.

1-[2-(1,3-Benzodioxolan-5-Yloxy)Phenyl]-4-[3-(6-Chloro-1H-Indol-3-Yl)Propyl]Piperazine, Dihydrochloride (2c). Mp: 165° C. (decomposition). $^1$H NMR (250 MHz, DMSO-$d_6$): 2.08 (m, 2H); 2.73 (t, 2H); 3.02 (m, 2H); 3.15 (m, 4H); 3.55 (t, 4H); 6.00 (s, 2H); 6.40 (d, 1H); 6.65 (s, 1H); 6.80 (d,1H), 6.85 (d, 1H); 7.00 (m, 2H); 7.05 (m, 2H); 7.25 (d, 1H); 7.38 (s, 1H); 7.55 (dd, 1H); 10.45 (s, 1H); 11.00 (s, 1H). MS (m/z): 490 (MH+). Anal. Calcd. for $C_{28}H_{30}Cl_3N_3O_3$: C, 59.73; H, 5.38; N, 7.47. Found C, 59.13; H, 5.36; N, 7.26.

1-[2-(2-Methoxyphenoxy)Phenyl]-4-[3-(5-Fluoro-1H-Indol-3-Yl)Propyl]Piperazine, Dihydrochloride (2d). Mp: 183–189° C. $^1$H NMR (500 MHz, DMSO-$d_6$): 2.12 (m, 2H); 2.73 (t, 2H); 3.05–3.25 (m, 6H); 3.55 (d, 2H); 3.65 (d, 2H); 3.75 (s, 3H); 6.53 (m, 1H); 6.88–7.20 (m, 9H); 7.27–7.40 (m, 3H); 11.05 (s, 2H). MS (m/z): 460 (MH+). Anal. Calcd. for $C_{28}H_{32}Cl_2FN_3O_2$: C, 63.16; H, 6.06; N, 7.89. Found C, 63.04; H, 6.07; N, 7.88.

1-[2-(1,4-Benzodioxan-6-Yloxy)Phenyl]-4-[3-(1H-Indol-3-Yl)Propyl]Piperazine (2e). $^1$H NMR (250 MHz, CDCl$_3$): 1.90 (qui, 2H); 2.40–2.60 (m, 6H); 2.79 (t, 2H); 3.15 (t, 4H); 4.22 (s, 4H); 6.45 (m, 2H); 6.77 (d, 1H); 6.85–7.22 (m, 7H); 7.35 (d, 1H); 7.60 (d, 1H); 7.92 (s, 1H). MS (m/z): 470 (MH+).

1-[2-(1,4-Benzodioxan-5-Yloxy)Phenyl]-4-[3-(5-Fluoro-1H-Indol-3-Yl)Propyl]Piperazine (2f). $^1$H NMR (250 MHz, CDCl$_3$): 1.90 (qui, 2H); 2.38–2.53 (m, 6H); 2.73 (t, 2H); 3.16 (t, 4H); 4.26 (s, 4H); 6.38 (dd, 1H); 6.60–6.75 (m, 2H); 6.83–7.10 (m, 6H); 7.23–7.30 (m, 3H); 7.92 (s, 1H). LC/MS (m/z): 488 (MH+), Rt=2.53, purity 99.8%

1-[2-(1,4-Benzodioxan-5-Yloxy)Phenyl]-4-[3-(6-Chloro-1H-Indol-3-Yl)Propyl]Piperazine (2g). $^1$H NMR (250 MHz, CDCl$_3$): 1.90 (qui, 2H); 2.35–2.50 (m, 6H); 2.75 (t, 2H); 3.18 (t, 4H); 4.28 (s, 4H); 6.40 (dd, 1H); 6.60–6.75 (m, 3H); 6.80–7.08 (m, 6H); 7.32 (d, 1H); 7.50 (d, 1H); 7.95 (s, 1H). LC/MS (m/z): 504 (MH+), Rt=2.60, purity 99.6%

1-[2-(1,4-Benzodioxan-6-Yloxy)Phenyl]-4-[3-(6-Chloro-1H-Indol-3-Yl)Propyl]Piperazine (2h). $^1$H NMR (250 MHz, CDCl$_3$): 1.90 (qui, 2H); 2.35–2.55 (m, 6H); 2.75 (t, 2H); 3.15 (t, 4H); 4.23 (s, 4H); 6.45 (m, 2H); 6.78–6.15 (m, 7H); 7.32 (d, 1H), 7.50 (d, 1H); 7.92 (s, 1H). LC/MS (m/z): 504 (MH+), Rt=2.62, purity 99.7%

1-[2-(2-Methoxyphenoxy)Phenyl]-4-[3-(6-Chloro-1H-Indol-3-Yl)Propyl]Piperazine (2i). 6-Chloro-3-(3-{4-[2-(2-methoxy-phenoxy)-phenyl]-piperazin-1-yl}-propyl)-1H-indole $^1$H NMR (250 MHz, CDCl$_3$): 1.90 (qui, 2H); 2.35–2.50 (m, 6H); 2.73 (t, 2H); 3.19 (t, 4H); 3.83 (s, 3H); 6.70–7.08 (m, 10H); 7.32 (d, 1H), 7.49 (d, 1H); 7.94 (s, 1H). LC/MS (m/z): 476 (MH+), Rt=2.59, purity 99.8%

1-[2-(3-Methoxyphenoxy)Phenyl]-4-[3-(6-Chloro-1H-Indol-3-Yl)Propyl]Piperazine (2j). $^1$H NMR (250 MHz, CDCl$_3$): 1.89 (qui, 2H); 2.33–2.60 (m, 6H); 2.73 (t, 2H); 3.13 (t, 4H); 3.75 (s, 3H); 6.49 (m, 2H); 6.58 (dd, 1H); 6.95–7.20 (m, 7H); 7.32 (d, 1H), 7.49 (d, 1H); 7.92 (s, 1H). LC/MS (m/z): 476 (MH+), Rt=2.64, purity 99.7%

Example 3

1-[2-(2-Methoxyphenoxy)Phenyl]-4-[3-(1H-Indol-3-Yl) Propyl]Piperazine (3a)

4-[(4-Nitrophenoxy)carbonyloxymethyl)phenoxymethyl polystyrene (267.0 g, 235 mmol) was suspended in dry N,N-dimethylformamide (2 L). N-Methylmorpholine (238.0 g, 2.35 mol) and piperazine (102.0 g, 1.17 mol) were added and the mixture was stirred at room temperature for 16 hrs. The resin was filtered off and washed with N,N-dimethylformamide (2×1 L), tetrahydrofuran (2×1 L), water (1×500 mL), methanol (2×1 L), tetrahydrofuran (2×1 L), methanol (1×1 L). Finally, the resin was washed with dichloromethane (3×500 mL) and dried in vacuo (25° C., 36 hrs) to yield an almost colourless resin (240.0 g).

A part of the resin thus obtained (115.1 g, 92 mmol) was suspended in dry tetrahydrofuran (1.6 L) and $\eta^6$-1,2-dichlorobenzene-$\eta^5$-cyclopentadienyliron(II) hexafluorophosphate (76.0 g, 184 mmol) was added followed by potassium carbonate (50.9 g, 368 mmol). The reaction mixture was stirred at 60° C. for 16 hrs. After cooling to room temperature, the resin was filtered off and washed with tetrahydrofuran (2×500 mL), water (2×250 mL), tetrahydrofuran (2×500 mL), water (2×250 mL), methanol (2×250 mL), dichloromethane (2×500 mL), methanol (2×250 mL). Finally, the resin was washed with dichloromethane (3×500 mL) and dried in vacuo (25° C., 36 hrs) to yield a dark orange resin (142 g).

To a solution of 2-hydroxyanisole (2.2 g, 17.7 mmol) in tetrahydrofuran (50 mL) was carefully added neat sodium hydride (15.5 mmol) at room temperature (Caution: Generation of hydrogen). The mixture was stirred additional 30 min after the generation of hydrogen ceased. Subsequently, a part of the above obtained resin (2.8 g, 1.72 mmol) was added and the mixture was stirred at 40° C. for 12 hrs. After cooling to room temperature, the resin was filtered off and washed with tetrahydrofuran (2×50 mL), tetrahydrofuran/water (1:1) (2×50 mL), N,N-dimethylformamide (2×50 mL), water (2×50 mL), methanol (3×50 mL), tetrahydrofuran (3×50 mL), and subsequently with methanol and tetrahydrofuran (each 50 mL, 5 cycles). Finally, the resin was washed with dichloromethane (3×50 mL) and dried in vacuo (25° C., 12 hrs).

The thus obtained resin (3.0 g, 1.84 mmol) and a 0.5 M solution of 1,10-phenanthroline in a 3:1 mixture of pyridine/water (20 mL) was placed in a light-transparent reactor tube. For decomplexation, the suspension was vortexed and irradiated with visible light for 12 hrs. A very characteristic feature of the decomplexation step is the appearance of the intensive red colour of the liquid phase during irradiation. The resin was filtered off and washed with methanol (2×25 mL), water (2×25 ml) and tetrahydrofuran (3×25 mL) until the washing solutions kept colourless (5 cycles) and the irradiation procedure was repeated until decomplexation was complete (5 cycles). After complete decomplexation, the resin was washed with dichloromethane (3×25 mL) and dried in vacuo (25° C., 12 h).

The resin (approx. 2.5 g, 1.84 mmol) was suspended in a 1:1-mixture of trifluoroacetic acid and dichloromethane (25 mL) and stirred at room temperature for 2 hrs. The resin was filtered off and washed with methanol (1×5 mL) and dichloromethane (1×5 mL). The liquid phases were combined and the volatile solvents were evaporated to yield a dark brown oil (1.5 g)

The oil was dissolved in acetonitril (10 mL). To the thus obtained solution, potassium carbonate (46 mg, 0.33 mmmol) and 3-(3-bromopropyl)-1H-indole (33 mg, 0.14 mmol) were added and the mixture was heated at 70° C. for 12 hrs. Isocyanomethyl polystyrene (250 mg, 0.29 mmmol) was added and the mixture was slowly cooled to room temperature. The resin was filtered off and washed with methanol (1×2 mL) and dichloromethane (1×2 mL). The combined liquid phases were evaporated from volatile solvents to yield a dark brown oil. The crude product was purified by preparative reversed phase HPLC chromatography. The resulting solution was subsequently loaded on a pre-conditioned ion exchange column. The column was washed with methanol (4 mL) and acetonitrile (4 mL), followed by elution of the product with 4 N solution of ammonia in methanol (4.5 mL). Evaporation of the volatile solvents afforded the title compound 3a as yellow oil (66 mg). LC/MS (m/z) 442 (MH$^+$), Rt=4.15, purity: 93%.

The following compounds were prepared analogously:

1-(2-Phenoxyphenyl)-4-[4-(]H-indol-3-yl)butyl]piperazine (3b): LC/MS (m/z) 426 (MH$^+$), RT=4.36, purity: 79%.

1-[2-(1,3-Benzodioxolan-5-yloxy)phenyl]-4-[4-(]H-indol-3-yl)butyl]piperazine (3c): LC/MS (m/z) 470 (MH$^+$), RT=2.62, purity: 89%.

1-[2-(2-Methoxyphenoxy)phenyl]-4-[2-(6-chloro-1H-indol-3-yl)ethyl]piperazine (3d): LC/MS (m/z) 462 (MH$^+$), RT=4.35, purity: 76%.

1-[2-(1,3-Benzodioxolan-5-yloxy)phenyl]-4-[2-(6-chloro-1H-indol-3-yl)ethyl]piperazine (3e): LC/MS (m/z) 476 (MH$^+$), RT=2.64, purity: 89%.

1-[2-[3-(Dimethylamino)phenoxy]phenyl]-4-[2-(6-chloro-1H-indol-3-yl)ethyl]piperazine (3f): LC/MS (m/z) 475 (MH$^+$), RT=2.32, purity: 91%.

1-[2-(2-Methoxyphenoxy)phenyl]-4-[4-(1H-indol-3-yl)butyl]piperazine (3g): LC/MS (m/z) 456 (MH$^+$), RT=4.31, purity: 90%.

1-[2-(4-Methoxyphenoxy)phenyl]-4-[3-(]H-indol-3-yl)propyl]piperazine (3h): LC/MS (m/z) 442 (MH$^+$), RT=4.18, purity: 90%.

1-{2-[3-(Dimethylamino)phenoxy]phenyl}-4-[4-(1H-indol-3-yl)butyl]piperazine (3i): LC/MS (m/z) 469 (MH$^+$), RT=2.27, purity: 88%.

1-(2-Phenoxyphenyl)-4-[2-(6-chloro-1H-indol-3-yl)ethyl]piperazine (3j): LC/MS (m/z) 432 (MH$^+$), RT=4.40, purity: 70%.

Example 4

2-(4-Chlorobutyl)-1,3-Dioxolan-4-Ylmethoxymethyl Polystyrene (4a).

A 2 L round bottom flask was charged with 2,2-dimethyl-1,3-dioxolan-4-ylmethoxymethyl polystyrene (90 g, 72 mmol, commercially available as (±)-1-(2,3-isopropylidene) glycerol polystyrene from Calbiochem-Novabiochem, cat. no. 01-64-0291). Toluene (900 mL) followed by p-toluenesulfonic acid mono hydrate (5.0 g, 26 mmol), sodium sulfate (25 g), and 5-chloropentanal (25.5 g, 211 mmol) were added and the mixture was boiled under reflux for 12 hrs. The reflux condenser was replaced by a Dean-Stark apparatus and the mixture was boiled under reflux for an additional 3 hrs. After cooling of the reaction mixture to 60° C., the resin was filtered off and washed with toluene (200 mL), tetrahydrofuran/pyridine (1:1, 200 mL), tetrahydrofuran/water/pyridine (10:10:1, 200 mL), methanol (200 mL), water (200 mL), tetrahydrofuran (200 mL), dichloromethane (200 mL), methanol (3×200 mL), and dichloromethane (3×200 mL). The resin was dried in vacuo (55° C., 12 hrs) to yield the title compound 4a (97 g).

The following compounds were prepared analogously:

2-(3-Chloropropyl)-1,3-dioxolan-4-ylmethoxymethyl polystyrene (4b)

2-(5-Chloropentyl)-1,3-dioxolan-4-ylmethoxymethyl polystyrene (4c)

Example 5

1-[2-(1,4-Benzodioxan-5-Yloxy)Phenyl]-4-[3-(5-Fluoro-1H-Indol-3-Yl)Propyl]Piperazine (5a).

2-(3-Chlorobutyl)-1,3-dioxolan-4-ylmethoxymethyl polystyrene (70 g, 90.3 mmol) was suspended in dry N,N-dimethylformamide (700 mL). Sodium iodide (68 g, 452 mmol) was added followed by diisopropylethylamine (232 mL, 1.36 mol) and piperazine (117 g, 1.36 mol). The reaction mixture was heated at 80° C. under stirring for 12 hrs. After cooling to room temperature, the resin was filtered off and washed with N,N-dimethylformamide (3×500 mL), methanol (3×500 mL), tetrahydrofuran (3×500 mL), and subsequently with methanol and tetrahydrofuran (each 250 mL, 5 cycles). Finally, the resin was washed with dichloromethane (3×500 mL) and dried in vacuo (25° C., 36 hrs) to yield an almost colourless resin (76 g).

A part of the obtained resin (50 g, 60.6 mmol) was then suspended in dry tetrahydrofuran (600 mL). η$^6$-1,2-Dichlorobenzene-η$^5$-cyclopentadienyliron(II) hexafluorophosphate (48 g, 116.2 mmol) was added followed by potassium carbonate (32 g, 233 mmol). The reaction mixture was stirred at 60° C. for 12 hrs. After cooling to room temperature, the resin was filtered off and washed with tetrahydrofuran (2×500 mL), water (2×250 mL), tetrahydrofuran (2×500 mL), methanol (2×250 mL), dichloromethane (2×500 mL), methanol (2×250 mL). Finally, the resin was washed with dichloromethane (3×500 mL) and dried in vacuo (25° C., 36 hrs) to yield a dark orange resin (70 g).

To a solution of 5-hydroxy-1,4-benzodioxane (2.8 g, 18.4 mmol) in tetrahydrofuran (50 mL) was carefully added neat sodium hydride (15.5 mmol) at room temperature (Caution: Generation of hydrogen). The mixture was stirred for an additional 30 min after the generation of hydrogen ceased. Subsequently, a part of the above obtained resin (2.8 g, 2.3 mmol) was added and the mixture was stirred at 40° C. for 12 hrs. After cooling to room temperature, the resin was filtered off and washed with tetrahydrofuran (2×50 mL), tetrahydrofuran/water (1:1) (2×50 mL), N,N-dimethylformamide (2×50 mL), water (2×50 mL), methanol (3×50 mL), tetrahydrofuran (3×50 mL), and subsequently with methanol and tetrahydrofuran (each 50 mL, 5 cycles). Finally, the resin was washed with dichloromethane (3×50 mL) and dried in vacuo (25° C., 12 hrs).

A part of the obtained resin (200 mg, 0.15 mmol) and a 0.5 M solution of 1,10-phenanthroline in a (3:1)-mixture of pyridine/water (10 mL) was placed in a light-transparent reactor tube. The suspension was vortexed and irradiated for 12 hrs. A very characteristic feature of the decomplexation step is the appearance of the intensive red colour of the liquid phase during irradiation. The resin was filtered off and washed with methanol (2×10 mL), water (2×10 ml) and tetrahydrofuran (3×10 mL) until the washing solutions kept colourless (ca. 5 cycles) and the irradiation procedure was repeated until decomplexation was complete (ca. 4 cycles). After complete decomplexation, the resin was washed with dichloromethane (3×10 mL) and dried in vacuo (25° C., 12 hrs).

The obtained resin (160 mg, 0.15 mmol) and 4-fluorophenylhydrazine hydrochloride (35 mg, 0.21 mmol) were mixed in a reactor tube. A 0.5 M solution of anhydrous zinc chloride in acetic acid (1.5 mL) was added and the reaction tube was sealed. The reaction mixture was stirred for 12 hrs at 70° C. After cooling to room temperature, the reaction mixture was filtered and the residual resin washed with dimethyl sulfoxide (1.5 mL). Saturated aqueous sodium carbonate solution (1.5 mL) was added carefully to the combined filtrates(Caution: Generation of carbondioxide). The solution was loaded on a pre-conditioned reversed phase C-18 column. The column was washed with water (4 mL) and the product was eluted with methanol (4.5 mL). After evaporation of the volatile solvents, the crude product was purified by preparative reversed phase HPLC chromatography. The resulting solution was subsequently loaded on a pre-conditioned ion exchange column. The column was washed with methanol (4 mL) and acetonitrile (4 mL), followed by elution of the product with 4 N solution of ammonia in methanol (4.5 mL). Evaporation of the volatile solvents afforded the title compound 5a as yellow oil (2 mg). LC/MS (m/z) 488 (MH$^+$), Rt=4.22, purity: 84%.

The following compounds were prepared analogously:

1-(2-Phenoxyphenyl)-4-[3-(5-methyl-1H-indol-3-yl)propyl]piperazine (5b): LC/M S (m/z) 426 (MH$^+$), RT=4.44, purity: 88%.

1-[2-(2-Methoxyphenoxy)phenyl-4-[3-(5-chloro-1H-indol-3-yl)propyl]piperazine (5c): LC/MS (m/z) 476 (MH$^+$), RT=4.46, purity: 95%.

1-[2-(2-Methoxyphenoxy)phenyl]-4-[3-(5-bromo-1H-indol-3-yl)propyl]piperazine (5d): LC/MS (m/z) 522 (MH$^+$), RT=4.52, purity: 91%.

1-(2-Phenoxyphenyl)-4-[3-(1H-indol-3-yl)propyl]piperazine (5e): LC/MS (m/z) 412 (MH$^+$), RT=4.25, purity: 98%.

1-(2-Phenoxyphenyl)-4-[3-(5-fluoro-1H-indol-3-yl)propyl]piperazine (5f): LC/MS (m/z) 430 (MH$^+$), RT=4.32, purity: 96%.

1-(2-Phenoxyphenyl)-4-[3-(5-bromo-1H-indol-3-yl)propyl]piperazine (5g): LC/MS (m/z) 492 (MH$^+$), RT=4.60, purity: 84%.

1-[2-(2,6-Dimethoxyphenoxy)phenyl]-4-[3-(5-bromo-1H-indol-3-yl)propyl]piperazine (5h): LC/MS (m/z) 552 (MH$^+$), RT=4.49, purity: 86%.

1-[2-[3-(Dimethylamino)phenoxy]phenyl]-4-[3-(5-methyl-1H-indol-3-yl)propyl]piperazine (5i): LC/MS (m/z) 469 (MH$^+$), RT=3.73, purity: 86%.

1-(2-Phenoxyphenyl)-4-[3-(5-chloro-1H-indol-3-yl)propyl]piperazine (5j): LC/MS (m/z) 446 (MH$^+$), RT=4.52, purity: 88%.

1-[2-(1,3-Benzodioxolan-5-yloxy)phenyl]-4-[3-(5-methyl-1H-indol-3-yl)propyl]piperazine (5k): LC/MS (m/z) 470 (MH$^+$), RT=4.38, purity: 70%.

1-[2-(2-Methoxyphenoxy)phenyl]-4-[3-(5-fluoro-1H-indol-3-yl)propyl]piperazine (5l): LC/MS (m/z) 460 (MH$^+$), RT=4.24, purity: 87%.

1-[2-2-Methoxyphenoxy)phenyl]-4-[3-(7-chloro-1H-indol-3-yl)propyl]piperazine (5m): LC/MS (m/z) 476 (MH$^+$), RT=4.42, purity: 96%.

1-[2-(1,3-Benzodioxolan-5-yloxy)phenyl]-4-[3-(5-fluoro-1H-indol-3-yl)propyl]piperazine (5n): LC/MS (m/z) 474 (MH$^+$), RT=4.25, purity: 99%.

1-[2-(1,3-Benzodioxolan-5-yloxy)phenyl]-4-[3-(5-iodo-1H-indol-3-yl)propyl]piperazine (5o): LC/MS (m/z) 582 (MH$^+$), RT=4.58, purity: 85%.

1-(2-Phenoxyphenyl)-4-[3-(7-chloro-1H-indol-3-yl)propyl]piperazine (5p): LC/MS (m/z) 430 (MH$^+$), RT=4.38, purity: 87%.

1-(2-Phenoxyphenyl)-4-[3-(5,7-difluoro-1H-indol-3-yl)propyl]piperazine (5q): LC/MS (m/z) 448 (MH$^+$), RT=4.44, purity: 84%.

1-[2-(2-Methoxyphenoxy)phenyl]-4-[3-(7-bromo-1H-indol-3-yl)propyl]piperazine (5r): LC/MS (m/z) 520 (MH$^+$), RT=4.50, purity: 77%.

1–2-[3-(Dimethylamino)phenoxy]phenyl]-4-[3-(5-fluoro-1H-indol-3-yl)propyl]piperazine (5s): LC/MS (m/z) 473 (MH$^+$), RT=3.63, purity: 96%.

1-[2-(2-Methoxyphenoxy)phenyl]-4-[3-(5-iodo-1H-indol-3-yl)propyl]piperazine (5t): LC/MS (m/z) 568 (MH$^+$), RT=4.63, purity: 82%.

1-[2-(1,3-Benzodioxolan-5-yloxy)phenyl]-4-[3-(5-chloro-1H-indol-3-yl)propyl]piperazine (5u): LC/MS (m/z) 490 (MH$^+$), RT=4.45, purity: 90%.

1-[2-(2,6-Dimethoxyphenoxy)phenyl]-4-[3-(5-chloro-1H-indol-3-yl)propyl]piperazine (5v): LC/MS (m/z) 506 (MH$^+$), RT=4.46, purity: 83%.

1-[2-(1,3-Benzodioxolan-5-yloxy)phenyl]-4-[3-(1H-pyrrolo[3,2-h]-quinolin-3-yl)propyl]piperazine (5w): LC/MS (m/z) 507 (MH$^+$), RT=3.30, purity: 97%.

1-[2-(2-Methoxyphenoxy)phenyl]-4-[3-(5,7-difluoro-1H-indol-3-yl)propyl]piperazine (5x): LC/MS (m/z) 478 (MH$^+$), RT=4.36, purity: 75%.

1-(2-Phenoxyphenyl)-4-[3-(5-iodo-1H-indol-3-yl)propyl]piperazine (5y): LC/MS (m/z) 5.38 (MH$^+$), RT=4.69, purity: 92%.

1-[2-(2-Methoxyphenoxy)phenyl]-4-[3-(1H-pyrrolo[3,2-h]quinolin-3-yl)propyl]piperazine (5z): LC/MS (m/z) 493.2 (MH$^+$), RT=3.29, purity: 96%.

1-[2-(3-Methoxyphenoxy)phenyl]-4-[3-(1H-pyrrolo[3,2-h]quinolin-3-yl)propyl]piperazine (5aa): LC/MS (m/z) 493 (MH$^+$), RT=3.38, purity: 96%.

1-[2-(1,4-Benzodioxan-5-yloxy)phenyl]-4-[3-(5-methyl-1H-indol-3-yl)propyl]piperazine (5ab): LC/MS (m/z) 484 (MH$^+$), RT=4.35, purity: 84%.

1-[2-(2,6-Dimethoxyphenoxy)phenyl]-4-[3-(5-methyl-1H-indol-3-yl)propyl]piperazine (5ac): LC/MS (m/z) 486 (MH$^+$), RT=4.38, purity: 80%.

1-[2-(3-Methoxyphenoxy)phenyl]-4-[3-(1H-indol-3-yl)propyl]piperazine (5ad): LC/MS (m/z) 442 (MH$^+$), RT=4.25, purity: 85%.

1-[2-(1,4-Benzodioxan-5-yloxy)phenyl]-4-[3-(1H-indol-3-yl)propyl]piperazine (5ae): LC/MS (m/z) 471 (MH$^+$), RT=4.13, purity: 83%.

1-[2-(1,3-Benzodioxolan-5-yloxy)phenyl]-4-[3-(5-bromo-1H-indol-3-yl)propyl]piperazine (5af): LC/MS (m/z) 536 (MH$^+$), RT=4.49, purity: 88%.

1-{2-[3-(Morpholin-4-yl)phenoxy]phenyl}-4-[3-(5-fluoro-1H-indol-3-yl)propyl]piperazine (5ag): LC/MS (m/z) 515 (MH$^+$), RT=4.17, purity: 94%.

1-[2-(3-Methoxyphenoxy)phenyl]-4-[3-(5-chloro-1H-indol-3-yl)propyl]piperazine (5ah): LC/MS (m/z) 476 (MH$^+$), RT=4.53, purity: 92%.

1-[2-(3-Ethoxyphenoxy)phenyl]-4-[3-(5-methyl-1H-indol-3-yl)propyl]piperazine (5ai): LC/MS (m/z) 470 (MH$^+$), RT=4.68, purity: 85%.

1-[2-(2,6-Dimethoxyphenoxy)phenyl]-4-[3-(5-iodo-1H-indol-3-yl)propyl]piperazine (5aj): LC/MS (m/z) 598 (MH$^+$), RT=4.61, purity: 70%.

1-{2-[3-(Diethylamino)phenoxy]phenyl}-4-[3-(5-fluoro-1H-indol-3-yl)propyl]piperazine (5ak): LC/MS (m/z) 501 (MH$^+$), RT=3.18, purity: 87%.

1-[2-(2,6-Dimethoxyphenoxy)phenyl]-4-[3-(5-fluoro-1H-indol-3-yl)propyl]piperazine (5al): LC/MS (m/z) 490 (MH$^+$), RT=4.26, purity: 88%.

1-{2-[3-(Morpholin-4-yl)phenoxy]phenyl}-4-[3-(5-bromo-1H-indol-3-yl)propyl]piperazine (5am): LC/MS (m/z) 475 (MH$^+$), RT=4.42, purity: 78%.

1-{2-[3-(Morpholin-4-yl)phenoxy]phenyl}-4-[3-(5-chloro-1H-indol-3-yl)propyl]piperazine (5an): LC/MS (m/z) 531 (MH$^+$), RT=4.34, purity: 81%.

1-{2-[3-(Morphlolin-4-yl)phenoxy]phenyl}-4-[3-(5-iodo-1H-indol-3-yl)propyl]piperazine (5ao): LC/MS (m/z) 623 (MH⁺), RT=4.56, purity: 71%.

1-[2-(3-Methoxyphenoxy)phenyl]-4-[3-(7-fluoro-1H-indol-3-yl)propyl]piperazine (5aq): LC/MS (m/z) 460 (MH⁺), RT=4.38, purity: 70%.

1-(2-Phenoxyphenyl)-4-[3-(5,7-dimethyl-1H-indol-3-yl)propyl]piperazine (5ar): LC/MS (m/z) 440 (MH⁺), RT=4.64, purity: 78%.

1-[2-(1,3-Benzodioxolan-5-yloxy)phenyl]-4-[3-(7-bromo-1H-indol-3-yl)propyl]piperazine (5as): LC/MS (m/z) 534 (MH⁺), RT=4.46, purity: 75%.

1-[2-(3,4,5-Trimethoxyphenoxy)phenyl]-4-[3-(5-bromo-1H-indol-3-yl)propyl]piperazine (5at): LC/MS (m/z) 580 (MH⁺), RT=4.34, purity: 81%.

Pharmacological Testing

The compounds of the invention were tested in well-recognised and reliable methods. The tests were as follows:

Inhibition of the Binding of ³H-YM-09151-2 to Human Dopamine D₄ Receptors

By this method, the inhibition by drugs of the binding of [³H]YM-09151-2 (0.06 nM) to membranes of human cloned dopamine $D_{4.2}$ receptors expressed in CHO-cells is determined in vitro. Method modified from NEN Life Science Products, Inc., technical data certificate PC2533-10/96. The results are given in the following Table 1 as $IC_{50}$-values.

Inhibition of the Binding of [³H]-Spiperone to Human D₃ Receptors

By this method, the inhibition by drugs of the binding [³H]Spiperone (0.3 nM) to membranes of human cloned dopamine D₃ receptors expressed in CHO-cells is determined in vitro. Method modified from R. G. MacKenzie et al., *Eur. J. Pharm.-Mol. Pharm. Sec.*, 1994, 266, 79–85. The results are given in the following Table 1 as $IC_{50}$-values.

The affinity of the compounds of the invention to $5-HT_{1A}$ receptors was determined by measuring the inhibition of binding of a radioactive ligand at $5-HT_{1A}$ receptors as described in the following test:

Inhibition of ³H-5-CT Binding to Human $5-HT_{1A}$ Receptors.

By this method, the inhibition by drugs of the binding of the $5-HT_{1A}$ agonist ³H-5-carboxamido tryptamine (³H-5-CT) to cloned human $5-HT_{1A}$ receptors stably expressed in transfected HeLa cells (HA7) (Fargin, A. et al, *J. Biol. Chem.*, 1989, 264, 14848) is determined in vitro. The assay was performed as a modification of the method described by Harrington, M. A. et al, *J. Pharmacol. Exp. Ther.*, 1994, 268, 1098. Human $5-HT_{1A}$ receptors (40 μg of cell homogenate) were incubated for 15 minutes at 37° C. in 50 mM Tris buffer at pH 7.7 in the presence of ³H-5-CT. Non-specific binding was determined by including 10 μM of metergoline. The reaction was terminated by rapid filtration through Unifilter GF/B filters on a Tomtec Cell Harvester. Filters were counted in a Packard Top Counter. The results obtained are presented in table 1 below.

Inhibition of ³H-5-HT Uptake Into Rat Brain Synaptosomes

Using this method, the ability of drugs to inhibit the accumulation of ³H-5-HT into whole rat brain synaptosomes is determined in vitro. The assay was performed as described by Hyttel, J., *Psychopharmacology* 1978, 60, 13. The results obtained are presented in table 1:

TABLE 1

| Compound No. | Inhibition of ³H-5-CT Binding $IC_{50}$ (nM) | Inhibition of ³H-5-HT Uptake $IC_{50}$ (nM) |
|---|---|---|
| 1b | 7.8 | 130 |
| 2b | 16 | 2.8 |
| 3c | 16 | 27% inhibition af 100 nM |
| 3e | 24 | 40% inhibition at 100 nM |
| 5a | 19 | 14 |
| 5e | 10 | 13 |
| 5f | 10 | 4.8 |
| 5h | 10 | 55% inhibition at 100 nM |
| 5i | 10 | 46% inhibition at 100 nM |
| 5l | 13 | 4.7 |
| 5x | 18 | 33 |
| 5ae | 26 | 42% inhibition at 100 nM |
| 5ag | 26 | 23 |
| 5ai | 28 | 34% inhibition at 100 nM |

Accordingly, as the compounds of the invention show affinities in the described tests, they are considered useful in the treatment of affective disorders, such as depression, generalised anxiety disorder, panic disorder, obsessive compulsive disorders, social phobia, and eating disorders, psychosis and neurological disorders such as ischaemia and senile dementia.

What is claimed is:

1. A compound of formula I

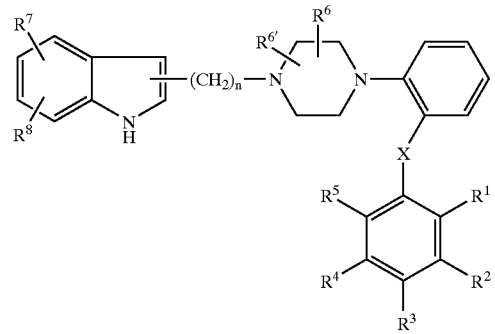

wherein

R⁷ and R⁸ independently represent hydrogen, halogen, $C_{1-6}$-alkyl;

or R⁷ and R⁸ together form a pyridyl-ring fused to the benzene ring;

R⁶ and R⁶' represent H or $C_{1-6}$-alkyl;

X represents -O- or -S-;

n is 2, 3, 4 or 5;

R¹, R², R³, R⁴ and R⁵ are independently selected from a group consisting of hydrogen, halogen, $C_{1-6}$-alkyl, $C_{2-6}$-alkenyl, $C_{2-6}$-alkynyl, $C_{3-8}$-cycloalkyl, aryl, hydroxy, hydroxy-$C_{1-6}$-alkyl, $C_{1-6}$-alkoxy, $C_{3-8}$-cycloalkoxy, $C_{1-6}$-alkylsulfanyl, acyl, NR⁹R¹⁰ wherein R⁹ and R¹⁰ independently represent hydrogen, $C_{1-6}$-alkyl, $C_{2-6}$-alkenyl, $C_{2-6}$-alkynyl, $C_{3-8}$-cycloalkyl aryl, hydroxy, hydroxyl $C_{1-6}$-alkyl, $C_{1-6}$-alkoxy, $C_{3-8}$-cycloalkoxy, $C_{1-6}$-alkylsulfanyl, acyl, NR⁹R¹⁰ wherein R⁹ and R¹⁰ independently represent hydrogen, $C_{1-6}$-alkyl, $C_{2-6}$-alkenyl, $C_{2-6}$-alkynyl, $C_{3-8}$-cycloalkyl or aryl; or R⁹ and R¹⁰ together with the nitrogen to which they are attached form a 1-morpholinyl, 1-piperidinyl, 1-homopiperidinyl, 1-piperazinyl, 1-homopiperazinyl, 1-imidazolyl, 1-pyrrolyl, or pyrazolyl, all of which may be further substituted with $C_{1-6}$-alkyl;

or two adjacent substituents of R¹-R⁵ together form a ring fused to the phenyl ring selected from the group consisting of:

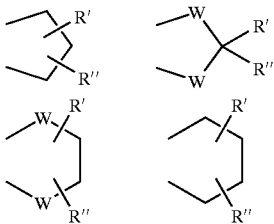

wherein W is O or S, and R' and R" are hydrogen or $C_{1-6}$-alkyl; or a pharmaceutically acceptable acid addition salt thereof.

2. The compound of claim 1 wherein n is 2,3 or 4.

3. The compound of claim 1 wherein $R^6$ and $R^{6'}$ are both hydrogen.

4. The compound of claim 1 wherein $R^1$, $R^2$, $R^3$, $R^4$ and $R^5$ are independently selected from hydrogen, alkoxy, $NR^9R^{10}$ wherein $R^9$ and $R^{10}$ independently represent hydrogen, $C_{1-6}$-alkyl; or $R^9$ and $R^{10}$ together form a 1-morpholino; or two of adjacent of $R^1$, $R^2$, $R^3$, $R^4$ and $R^5$ together form a fused ring consisting of —O—CH₂—O——O—CH₂—CH₂—O—, or —CH₂—CH₂—CH₂—.

5. The compound of claim 1 wherein one or two of $R^1$, $R^2$, $R^3$, $R^4$ and $R^5$ are not hydrogen.

6. The compound of claim 1 which is selected from the group consisting of 1-{1-[3-(dimethylamino)phenoxy]phenyl}-4- [2-(1H-indol-3-yl)ethyl]piperazine; 1-[1-(1,3-Benzodioxolan-5-yloxy)phenyl]-4-[2-(1H-indol-3-yl)ethyl]piperazine; 1-{1-[3-(dimethylamino)phenoxy]phenyl}-4-[3-(1H-indol-3-yl)propyl]piperazine; 1-[1-(1,3-Benzodioxolan-5-yloxy)phenyl]-4-[3-(1H-indol-3-yl)propyl]piperazine; 1-[2-(1,3-Benzodioxolan-5-yloxy)phenyl]-4-[3-(6-chloro-1H-indol-3-yl)propyl]piperazine, 1-[2-(2-Methoxyphenoxy)phenyl]-4-[3-(5-fluoro-1H-indol-3-yl)propyl]piperazine; 1-[2-(1,4-Benzodioxan-6-yloxy)phenyl]-4-[3-(1H-indol-3-yl)propyl]piperazine; 1-[2-(1,4-Benzodioxan-5-yloxy)phenyl]-4-[3-(5-fluoro-1H-indol-3-yl)propyl]piperazine; 1-[2-(1,4-Benzodioxan-5-yloxy)phenyl]-4-[3-(6-chloro-1H-indol-3-yl)propyl]piperazine; 1-[2-(1,4-Benzodioxan-6-yloxy)phenyl]-4-[3-(6-chloro-1H-indol-3-yl)propyl]piperazine; 1-[2-(2-Methoxyphenoxy)phenyl]-4-[3-(6-chloro-1H-indol-3-yl)propyl]piperazine; 1-[2-(3-Methoxyphenoxy)phenyl]-4-[3-(6-chloro-1H-indol-3-yl)propyl]piperazine; 1-[2-(2-Methoxyphenoxy)phenyl]-4-[3-(1H-indol-3-yl)propyl]piperazine; 1-(2-Phenoxyphenyl)-4-[4-(1H-indol-3-yl)butyl]piperazine; 1-[2-(1,3-Benzodioxolan-5-yloxy)phenyl]-4-[4-(1H-indol-3-yl)butyl]piperazine; 1-[2-(2-Methoxyphenoxy)phenyl]-4-[2-(6-chloro-1H-indol-3-yl)ethyl]piperazine; 1-[2-(1,3-Benzodioxolan-5-yloxy)phenyl]-4-[2-(6-chloro-1H-indol-3-yl)ethyl]piperazine; 1-[2-(3-(Dimethylamino)phenoxy)phenyl]-4-[2-(6-chloro-1H-indol-3-yl)ethyl]piperazine; 1-[2-(2-Methoxyphenoxy)phenyl]-4-[4-(1H-indol-3-yl)butyl]piperazine; 1-[2-(4-Methoxyphenoxy)phenyl]-4-[3-(1H-indol-3-yl)propyl]piperazine; 1-[2-(3-(Dimethylamino)phenoxy)phenyl]-4-[4-(1H-indol-3-yl)butyl]piperazine; 1-(2-Phenoxyphenyl)-4-[2-(6-chloro-1H-indol-3-yl)ethyl]piperazine; 1-[2-(1,4-Benzodioxan-5-yloxy)phenyl]-4-[3-(5-fluoro-1H-indol-3-yl)propyl]piperazine; 1-(2-Phenoxyphenyl)-4-[3-(5-methyl-1H-indol-3-yl)propyl]piperazine; 1-[2-(2-Methoxyphenoxy)phenyl]-4-[3-(5-chloro-1H-indol-3-yl)propyl]piperazine; 1-[2-(2-Methoxyphenoxy)phenyl]-4-[3-(5-bromo-1H-indol-3-yl)propyl]piperazine; 1-(2-Phenoxyphenyl)-4-[3-(1H-indol-3-yl)propyl]piperazine; 1-(2-Phenoxyphenyl)-4-[3-(5-fluoro-1H-indol-3-yl)propyl]piperazine; 1-(2-Phenoxyphenyl)-4-[3-(5-bromo-1H-indol-3-yl)propyl]piperazine; 1-[2-(2,6-Dimethoxyphenoxy)phenyl]-4-[3-(5-bromo-1H-indol-3-yl)propyl]piperazine; 1-[2-(3-(Dimethylamino)phenoxy)phenyl]-4-[3-(5-methyl-1H-indol-3-yl)propyl]piperazine; 1-(2-Phenoxyphenyl)-4-[3-(5-chloro-1H-indol-3-yl)propyl]piperazine; 1-[2-(1,3-Benzodioxolan-5-yloxy)phenyl]-4-[3-(5-methyl-1H-indol-3-yl)propyl]piperazine; 1-[2-(2-Methoxyphenoxy)phenyl]-4-[3-(5-fluoro-1H-indol-3-yl)propyl]piperazine; 1-[2-(2-Methoxyphenoxy)phenyl]-4-[3-(7-chloro-1H-indol-3-yl)propyl]piperazine; 1-[2-(1,3-Benzodioxolan-5-yloxy)phenyl]-4-[3-(5-fluoro-1H-indol-3-yl)propyl]piperazine; 1-[2-(1,3-Benzodioxolan-5-yloxy)phenyl]-4-[3-(5-iodo-1H-indol-3-yl)propyl]piperazine; 1-(2-Phenoxyphenyl)-4-[3-(7-chloro-1H-indol-3-yl)propyl]piperazine; 1-(2-Phenoxyphenyl)-4-[3-(5,7-difluoro-1H-indol-3-yl)propyl]piperazine; 1-[2-(2-Methoxyphenoxy)phenyl]-4-[3-(7-bromo-1H-indol-3-yl)propyl]piperazine; 1-[2-(3-(Dimethylamino)phenoxy)phenyl]-4-[3-(5-fluoro-1H-indol-3-yl)propyl]piperazine; 1-[2-(2-Methoxyphenoxy)phenyl]-4-[3-(5-iodo-1H-indol-3-yl)propyl]piperazine; 1-[2-(1,3-Benzodioxolan-5-yloxy)phenyl]-4-[3-(5-chloro-1H-indol-3-yl)propyl]piperazine; 1-[2-(2,6-Dimethoxyphenoxy)phenyl]-4-[3-(5-chloro-1H-indol-3-yl)propyl]piperazine; 1-[2-(1,3-Benzodioxolan-5-yloxy)phenyl]-4-[3-(1H-pyrrolo[3,2-h]quinolin-3-yl)propyl]piperazine; 1-[2-(2-Methoxyphenoxy)phenyl]-4-[3-(5,7-difluoro-1H-indol-3-yl)propyl]piperazine; 1-(2-Phenoxyphenyl)-4-[3-(5-iodo-1H-indol-3-yl)propyl]piperazine; 1-[2-(2-Methoxyphenoxy)phenyl]-4-[3-(1H-pyrrolo[3,2-h]quinolin-3-yl)propyl]piperazine; 1-[2-(3-Methoxyphenoxy)phenyl]-4-[3-(1H-pyrrolo[3,2-h]quinolin-3-yl)propyl]piperazine; 1-[2-(1,4-Benzodioxan-5-yloxy)phenyl]-4-[3-(5-methyl-1H-indol-3-yl)propyl]piperazine; 1-[2-(2,6-Dimethoxyphenoxy)phenyl]-4-[3-(5-methyl-1H-indol-3-yl)propyl]piperazine; 1-[2-(3-Methoxyphenoxy)phenyl]-4-[3-(1H-indol-3-yl)propyl]piperazine; 1-[2-(1,4-Benzodioxan-5-yloxy)phenyl]-4-[3-(1H-indol-3-yl)propyl]piperazine; 1-[2-(1,3-Benzodioxolan-5-yloxy)phenyl]-4-[3-(5-bromo-1H-indol-3-yl)propyl]piperazine; 1-{2-[3-(Morpholin-4-yl)phenoxy]phenyl}-4-[3-(5-fluoro-1H-indol-3-yl)propyl]piperazine; 1-[2-(3-Methoxyphenoxy)phenyl]-4-[3-(5-chloro-1H-indol-3-yl)propyl]piperazine; 1-[2-(3-Ethoxyphenoxy)phenyl]-4-[3-(5-methyl-1H-indol-3-yl)propyl]piperazine; 1-[2-(2,6-Dimethoxyphenoxy)phenyl]-4-[3-(5-iodo-1H-indol-3-yl)propyl]piperazine; 1-[2-(3-(Diethylamino)phenoxy)phenyl]-4-[3-(5-fluoro-1H-indol-3-yl)propyl]piperazine; 1-[2-(2,6-Dimethoxyphenoxy)phenyl]-4-[3-(5-fluoro-1H-indol-3-yl)propyl]piperazine; 1-{2-[3-(Morpholin-4-yl)phenoxy]phenyl}-4-[3-(5-bromo-1H-indol-3-yl)propyl]piperazine; 1-{2-[3-(Morpholin-4-yl)phenoxy]phenyl}-4-[3-(5-chloro-1H-indol-3-yl)propyl]piperazine; 1-{2-[3-(Morpholin-4-yl)phenoxy]phenyl}-4-[3-(5-iodo-1H-indol-3-yl)propyl]piperazine; 1-[2-(3-Methoxyphenoxy)phenyl]-4-[3-(7-fluoro-1H-indol-3-yl)propyl]piperazine; 1-(2-Phenoxyphenyl)-4-[3-(5,7-dimethyl-1H-indol-3-yl)propyl]piperazine; 1-[2-(1,3-Benzodioxolan-5-yloxy)phenyl]-4-[3-(7-bromo-1H-indol-3-yl)propyl]piperazine; and 1-[2-(3,4,5-Trimethoxyphenoxy)phenyl]-4-[3-(5-bromo-1H-indol-3-yl)propyl]piperazine.

7. A pharmaceutical composition comprising at least one compound of claim 1 or a pharmaceutically acceptable acid addition salt in a therapeutically effective amount, in combination with one or more pharmaceutically acceptable carriers or diluents.

8. A method for the treatment of affective or neurological diseases in humans wherein said disease or disorder is selected from the group consisting of depression, psychosis, generalized anxiety disorder, panic disorder, and obsessive compulsive disorder, impulse control disorder, and social phobia comprising administering an effective amount of a compound of claim 1 to a patient in need thereof.

* * * * *